US00PP17669P3

(12) United States Plant Patent
Sato

(10) Patent No.: US PP17,669 P3
(45) Date of Patent: May 1, 2007

(54) **PLANT VARIETY OF *LOROPETALUM CHINENSE* VAR. *RUBRUM* NAMED 'SATO'S DWARF RED'**

(50) Latin Name: ***Loropetalum chinense* var. *rubrum* Yieh**
Varietal Denomination: Sato's Dwarf Red

(75) Inventor: Noboru Sato, Saitama Prefecture (JP)

(73) Assignee: Hines Nurseries, Inc., Irvine, CA (US)

( * ) Notice: Subject to any disclaimer, the term of this patent is extended or adjusted under 35 U.S.C. 154(b) by 74 days.

(21) Appl. No.: 11/000,544

(22) Filed: Nov. 30, 2004

(65) Prior Publication Data

US 2006/0117431 P1 Jun. 1, 2006

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—Annette H Para
(74) *Attorney, Agent, or Firm*—Christie, Parker & Hale, LLP

(57) ABSTRACT

A new plant variety of *Loropetalum chinese* var. *rubrum* named 'Sato's Dwarf Red', having a low growing, compact habit and red foliage throughout the year.

1 Drawing Sheet

Figure 1:
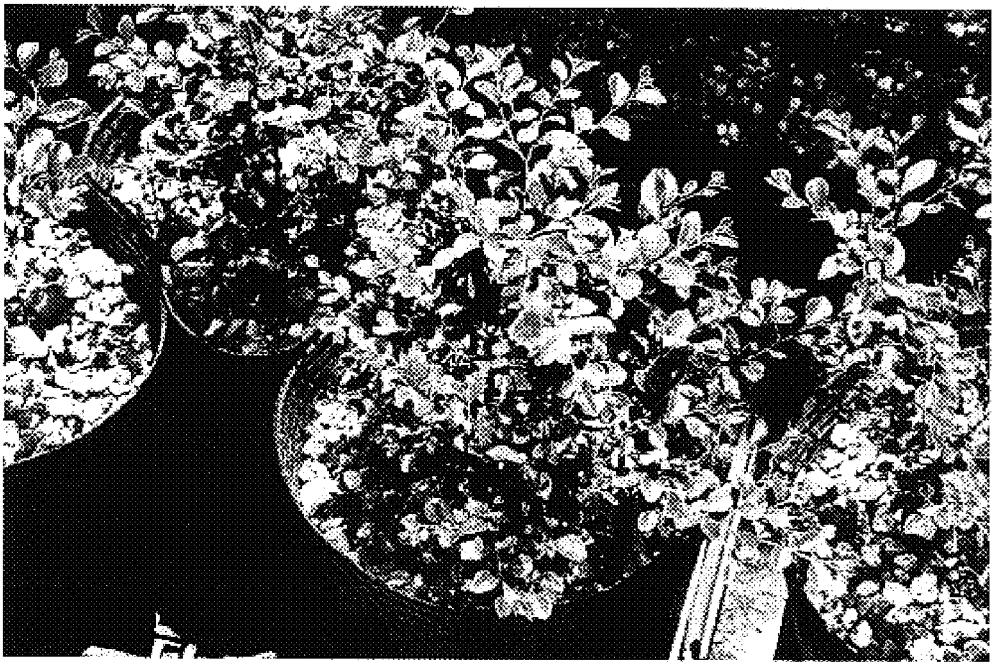

Botanical classification: *Loropetalum chinense* var. *rubrum* Yieh.
Varietal name: 'Sato's Dwarf Red'.

BACKGROUND OF THE INVENTION

The present invention relates to a new and distinct variety of *Loropetalum chinense* var. *rubrum* and was developed in a controlled breeding program in Angyo Kichi Zo, Saitama Prefecture, Japan by the originator Mr. Noboru Sato. The varietal denomination of the new variety is 'Sato's Dwarf Red'.

The genus *Loropetalum* is included in the family Hamamelidaceae that comprises about 15 genera of shrubs and trees growing in the northern hemisphere. *Loropetalum* comprises one species of evergreen shrub or small tree, which possesses desirable ornamental characteristics. *Loropetalum* was first introduced to Europe as an ornamental plant in the 1880s, and is believed to have been cultivated in North America since the early 1930s.

*Loropetalum chinense* is a native of China, and was first discovered in 1928 in Hunan province. It was rediscovered in the late 1980s and subsequently introduced to the United States. *Loropetalum chinense* generally has alternate, ovate leaves to 6 cm. long and 3 cm. wide. The plant is evergreen or partly evergreen depending on winter temperature. Leaf color ranges from light to dark burgundy, occasionally green, depending on light intensity, cultural conditions and cultivar. Shoots are slender, brown, and densely pubescent, pit is solid. Leaves are generally densely pubescent overall.

Flowers of *Loropetalum chinense* are perfect, four strap like, about 2 cm. long, and about 0.3 cm. wide petals. Three to six flowers are together in each leaf axil. Pedicel and calyx have a white pubescence. Flower color is pinkish to reddish purple depending on the cultivar. Flowering is heaviest in early spring.

SUMMARY OF THE INVENTION

The new variety was discovered as a open pollinated seedling in a controlled planting of *Loropetalum chinense* var. *rubrum* (unnamed, unpatented) and differs from other cultivars known to the inventor, including its parents, in having a low growing, compact habit and red foliage throughout the plant year. Asexual reproduction of the new variety by stem cuttings performed in Kawaguchi City, Saitama Prefecture, Japan has confirmed that the distinctive characteristics of the new variety are stable and reproduced true to type in successive generations of asexual propagation.

COMPARISON WITH PARENTS AND COMPARABLE VARIETIES

'Sato's Dwarf Red' is distinguished from its parents and all other varieties of *Loropetalum chinense* of which I am aware by its prostrate, compact habit, reaching no more than 60 cm in height and 90 to 180 cm in width, and its year-round burgundy red foliage. 'Sato's Dwarf Red' can be compared with *Loropetalum chinense* var. *rubrum* 'Hindwarf' (U.S. Plant Pat. No. 12,203); 'Hindwarf' is approximately the same size and habit as 'Sato's Dwarf Red', but the mature foliage of 'Hindwarf' turns dark green in color while 'Sato's Dwarf Red' maintains its burgundy red foliage into maturity. 'Sato's Dwarf Red' can also can be compared with *Loropetalum chinense* var. *rubrum* 'Ruby' (unpatented); 'Ruby' matures to approximately about 120 cm high and about 90 cm wide. 'Sato's Dwarf Red' also can be compared with *Loropetalum chinense* var. *rubrum* 'Hines Purpleleaf' (unpatented), which reaches about 4.5 m high and about 3.5 m wide at maturity.

BRIEF DESCRIPTION OF ILLUSTRATIONS

The accompanying illustrations show a specimen of the new cultivar in a photo illustration as true to color as is reasonably possible to make in an illustration of this character.

FIG. 1 illustrates the new variety in a No. 1 nursery container; young and mature foliage are visible.

DETAILED DESCRIPTION OF THE NEW VARIETY

*Loropetalum chinense* var. *rubrum* 'Sato's Dwarf Red' has not been observed under all possible environmental, cultural, and light conditions. The following observations and descriptions are of plants grown in containers at Lewisberry, Pa., and Angyo Kichi Zo, Saitama Prefecture, Japan. Phenotypic expression may vary with light intensity, cultural, and environmental conditions. In this description, color references are to The Royal Horticultural Society Colour Chart (2001) and terminology used in this color chart. As with many plants in the Hamamelidaceae family, phenotypic characteristics can be dramatically different in terms of growth morphology. For example, viewing this plant in Vacaville, Calif., the growth habit is distinctly pendulous, growing down the pot and tending to have a horizontal growth form.

Classification:

*Botanical.*—*Loropetalum chinense* var. *rubrum* Yieh 'Sato's Dwarf Red'.

*Parentage.*—Mother Plant: *Loropetalum chinense* var. *rubrum* (unnamed, unpatented). Father Plant: *Loropetalum chinense* var. *rubrum* (unnamed, unpatented).

*Propagation.*—By vegetative cuttings.

Plant:

*Typical size.*—To 60 cm in height and 180 cm in width.

*Habit.*—Prostrate to mounding branching habit.

*Hardiness.*—USDA Zone 7 (0 degree. F. to 7.degree. F.).

*Vigor.*—Moderate.

*Pests/diseases.*—No pest or disease problems noted.

Branches:

*Branching.*—Densely branched.

*Lateral branches.*—Multi-branched shrub.

*Branch size.*—Typical branch about 1 m. long, pendulous.

*Branch diameter.*—Typical branch about 1 cm. in diameter; branch apex is typically about 1 mm. or less in diameter.

*Branch color.*—Near Grayed-Orange Group 177A.

Leaf:

*Arrangement.*—Simple, alternate.

*Shape.*—Ovate.

*Leaf size.*—About 1 to 2.5 cm. long; 1 to 1.5 cm. wide.

*Leaf apex.*—Acute to obtuse.

*Leaf base.*—Obtuse to acute; occasionally unequal.

*Leaf margin.*—Entire, with stellate hairs.

*Leaf texture/substance.*—Firm to leathery; upper surface and glossy, with impressed veins; underside glaucous with greenish veins and whitish midrib, with scattered stellate hairs.

*Leaf color.*—Varies with intensity of sunlight and cultural conditions; the following color readings were taken in August of plants grown in full sun conditions.

*New foliage.*—Upper Side: Near Greyed-Purple Group 185 A–B. Under Side: Near Red-Purple Group 60A–B.

*Mature foliage.*—Upper Side: Near Greyed-Purple Group 183A–B. Under Side: Near Greyed-Green Group 186A–B.

*Venation.*—Upper Surface: Pinnate. Under Surface: Pinnate.

*Venation color.*—New Foliage Upper Surface: Near Greyed-Purple Group 185A–B. Under Surface: Near Red-Purple Group 60A–B. Mature Foliage Upper Surface: Near Greyed-Purple Group 183A–B. Under Surface: Near Greyed-Green Group 186A–B.

*Petioles.*—Size: Approximately 1 to 3 mm long; approximately 0.8 mm wide. Color: Near Greyed-Orange Group 177B–C (upper and lower surfaces).

*Internodes.*—Approximately 0.5 to 1.5 cm.

Inflorescence:

*Bloom period.*—Early spring with occasional light repeat blooming throughout the growing season.

*Flower form.*—Perfect, about 8 to 11 pinkish colored strap-like petals per flower.

*Flower arrangement.*—Congested terminal raceme on short peduncle, occasionally solitary at terminals or in leaf axils; about 6 to 8 flowers per inflorescence.

*Flower size.*—Approximately 1.5 to 2.0 cm long and about 1 to 2 mm wide.

*Diameter.*—Approximately 8 mm.

*Depth.*—About 8 mm.

*Lastingness of individual blooms.*—Between 2 and 3 weeks.

*Fragrance.*—None noted.

*Petals.*—Color Upper Surface: From near Red Group 55B to 51A, 53C, 52A and 53D. Lower Surface: From near Red group 55B and 51A, 52A and 53D. Length/Width: About 1.5 cm long and about 1 mm wide. Apex: Flat. Margin: Smooth.

*Buds.*—Length: Approximately 3 mm. Diameter: Approximately 2 mm. Color: Near Red-Purple Group 60B.

*Peduncles.*—Length: Approximately 1 mm. Diameter: Approximately 0.5 mm. Color: Light brown.

Reproductive organs:

*Stamens.*—4.

*Stigma.*—1.

*Pistils.*—1.

*Pollen.*—Amount Produced: Minute. Color: Off-white.

*Fruit.*—Type: Ovoid, woody, 2-horned capsule, one seed per each cell. Amount: About 75 to 100 per plant per year. Length: About 5 mm. Diameter: About 6 mm. Color: Dark brown.

It is claimed:

1. A new and distinct variety of *Loropetalum chinense* var. *rubrum* plant substantially as shown and described.

* * * * *